US012573115B2

(12) United States Patent (10) Patent No.: US 12,573,115 B2
Weiss et al. (45) Date of Patent: *Mar. 10, 2026

(54) SYSTEMS, METHODS, AND DEVICES FOR GENERATING A CORRECTED IMAGE

(71) Applicant: Mazor Robotics Ltd., Caesarea (IL)

(72) Inventors: Noam Weiss, Haifa (IL); Ben Yosef Hai Ezair, Haifa (IL)

(73) Assignee: Mazor Robotics Ltd., Caesarea (IL)

( * ) Notice: Subject to any disclaimer, the term of this patent is extended or adjusted under 35 U.S.C. 154(b) by 93 days.

This patent is subject to a terminal disclaimer.

(21) Appl. No.: 18/237,801

(22) Filed: Aug. 24, 2023

(65) Prior Publication Data

US 2023/0401766 A1 Dec. 14, 2023

Related U.S. Application Data

(63) Continuation-in-part of application No. 18/203,463, filed on May 30, 2023, now Pat. No. 12,067,653, which is a continuation of application No. 17/464,410, filed on Sep. 1, 2021, now Pat. No. 11,763,499.

(51) Int. Cl.
G06T 11/00 (2006.01)
A61B 6/02 (2006.01)

(52) U.S. Cl.
CPC ............ G06T 11/005 (2013.01); A61B 6/027 (2013.01)

(58) Field of Classification Search
CPC .............................. A61B 6/027; G06T 11/005
See application file for complete search history.

(56) References Cited

U.S. PATENT DOCUMENTS

| | | | |
|---|---|---|---|
| 4,894,855 A | 1/1990 | Kresse | |
| 7,551,716 B2 | 6/2009 | Ruhrnschopf | |
| 9,265,475 B2 | 2/2016 | Yang et al. | |
| 9,285,327 B2 | 3/2016 | Ying | |
| 10,561,384 B2 | 2/2020 | Tanaka et al. | |
| 10,788,595 B2 | 9/2020 | Alving et al. | |
| 11,763,499 B2 | 9/2023 | Weiss et al. | |

(Continued)

FOREIGN PATENT DOCUMENTS

WO WO 2013/190440 12/2013

OTHER PUBLICATIONS

International Search Report and Written Opinion for International (PCT) Patent Application No. PCT/IL2022/050946, dated Nov. 25, 2022, 10 pages.

(Continued)

*Primary Examiner* — Blake C Riddick
(74) *Attorney, Agent, or Firm* — Sheridan Ross P.C.

(57) ABSTRACT

Systems, methods, and devices for generating a corrected image are provided. A first robotic arm may be configured to orient a source at a first pose and a second robotic arm may be configured to orient a detector at a plurality of second poses. An image dataset may be received from the detector at each of the plurality of second poses to yield a plurality of image datasets. The plurality of datasets may comprise an initial image having a scatter effect. The plurality of image datasets may be saved. A scatter correction may be determined and configured to correct the scatter effect. The correction may be applied to the initial image to correct the scatter effect.

20 Claims, 7 Drawing Sheets

(56) References Cited

U.S. PATENT DOCUMENTS

| | | | |
|---|---|---|---|
| 2009/0310754 A1 | 12/2009 | Timmer et al. | |
| 2010/0119139 A1 | 5/2010 | Bertram et al. | |
| 2010/0266171 A1* | 10/2010 | Wendler .............. | A61B 6/5205 |
| | | | 382/128 |
| 2012/0014618 A1 | 1/2012 | Sun et al. | |
| 2012/0163531 A1 | 6/2012 | Zhang et al. | |
| 2014/0163368 A1 | 6/2014 | Rousso et al. | |
| 2020/0121267 A1 | 4/2020 | Deutschmann | |
| 2020/0175733 A1* | 6/2020 | Yu ......................... | G06T 11/005 |
| 2021/0369378 A1 | 12/2021 | Ofer et al. | |
| 2022/0087624 A1 | 3/2022 | Quinlan et al. | |
| 2022/0395342 A1 | 12/2022 | Weiss et al. | |

OTHER PUBLICATIONS

Notice of Allowance for U.S. Appl. No. 17/464,410, dated Feb. 27, 2023, 10 pages.

Official Action for U.S. Appl. No. 18/203,463, dated Dec. 14, 2023, 9 pages.

Notice of Allowance for U.S. Appl. No. 18/203,463, dated Apr. 3, 2024, 9 pages.

Extended Search Report for European Patent Application No. 25198135.3, dated Dec. 11, 2025, 8 pages.

* cited by examiner

300

302 — Image dataset(s)

304 — Scatter correction model

306 — Scatter correction

312 — Image

308 — Image processing model

310 — Corrected image

600

404 — Receive an image dataset from a detector at each of a plurality of second poses to yield a plurality of image datasets 408 — Store the plurality of image datasets 412 — Train a machine learning model 416 — Determine a scatter correction configured to correct the scatter effect 420 — Apply the correction to an image 424 — Calculate a magnification factor 428 — Scale the initial image

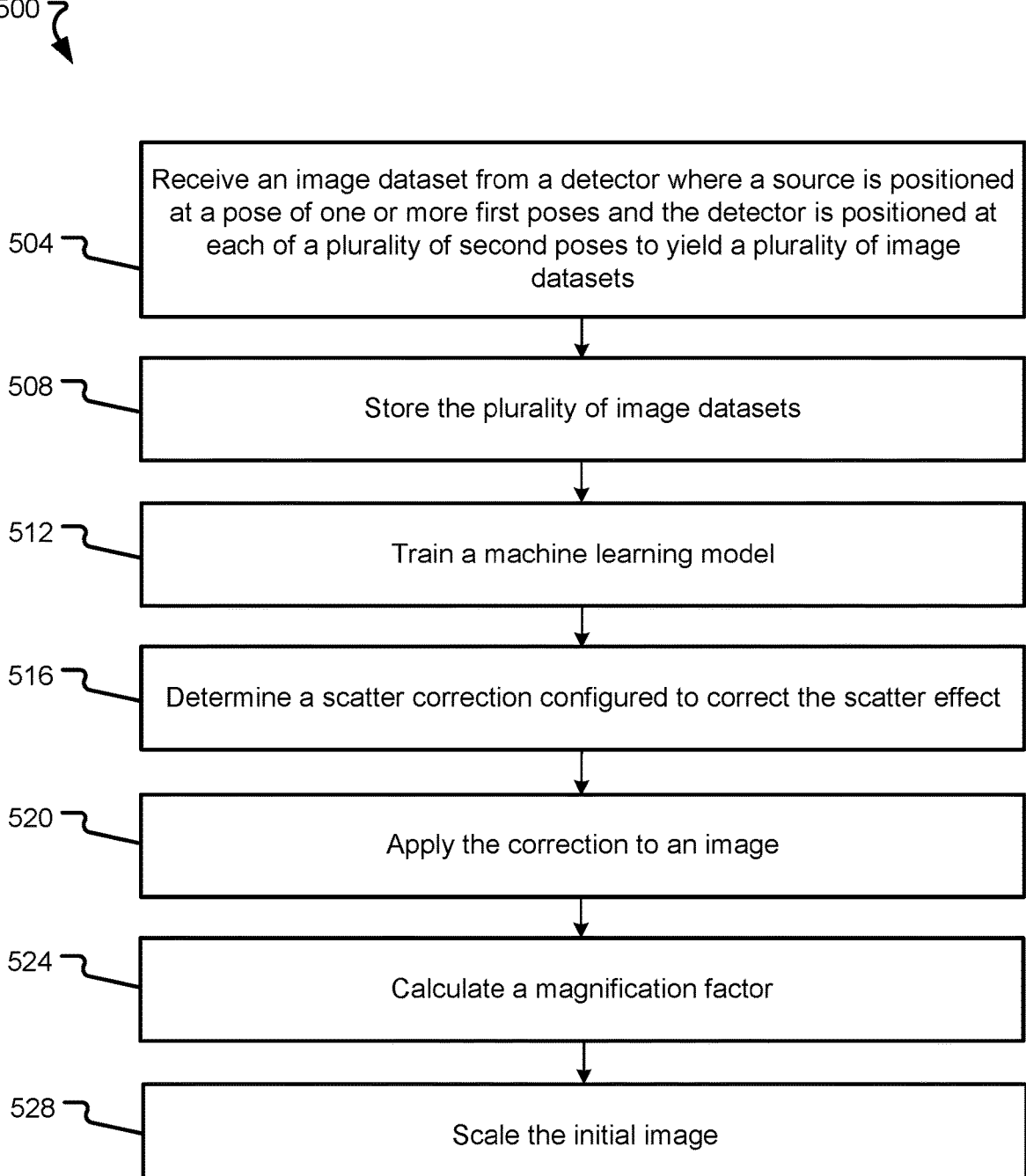

500

504 — Receive an image dataset from a detector where a source is positioned at a pose of one or more first poses and the detector is positioned at each of a plurality of second poses to yield a plurality of image datasets 508 — Store the plurality of image datasets 512 — Train a machine learning model 516 — Determine a scatter correction configured to correct the scatter effect 520 — Apply the correction to an image 524 — Calculate a magnification factor 528 — Scale the initial image

FIG. 5

SYSTEMS, METHODS, AND DEVICES FOR GENERATING A CORRECTED IMAGE

CROSS-REFERENCE TO RELATED APPLICATIONS

This application is a continuation-in-part of U.S. application Ser. No. 18/203,463, filed on May 30, 2023, which is a continuation of U.S. application Ser. No. 17/464,410, filed on Sep. 1, 2021, each of which applications are incorporated herein by reference in their entireties.

FIELD

The present technology generally relates to imaging and image processing, and relates more particularly to generating a corrected image using a scatter correction.

BACKGROUND

Imaging devices may be used by a medical provider for diagnostic and/or therapeutic purposes. Images (whether two-dimensional (2D) or three-dimensional (3D)) obtained from such imaging devices may include defects such as noise, oversaturation, and/or distortions. As such, hardware or software may be used to reduce such defects.

SUMMARY

Example aspects of the present disclosure include:

A system for generating a corrected image according to at least one embodiment of the present disclosure comprises an imaging device comprising a source configured to emit a wave and a detector configured to receive a signal indicative of the emitted wave; a first robotic arm configured to orient the source at a first pose; a second robotic arm configured to orient the detector at a plurality of second poses, wherein each second pose and the first pose define a source detector distance extending between the source and the detector; at least one processor; and a memory storing data for processing by the processor, the data, when processed, causing the processor to: receive an image dataset from the detector at each of the plurality of second poses to yield a plurality of image datasets, the plurality of datasets comprising an initial image having a scatter effect; save the plurality of image datasets; determine a scatter correction configured to correct the scatter effect; and applying the correction to the initial image to correct the scatter effect.

Any of the aspects herein, wherein the memory saves further data configured to cause the processor to: train a scatter correction model using a Monte-Carlo simulation to simulate a plurality of photon paths that forms an image, the image being at least one of a historical image or a simulated image, wherein determining the scatter correction uses the trained model.

Any of the aspects herein, wherein determining the scatter correction comprises providing the image dataset to a trained scatter correction model.

Any of the aspects herein, wherein the scatter correction model is trained using a plurality of image datasets and an output of the scatter correction model comprises a scatter correction.

Any of the aspects herein, wherein the scatter correction model is trained using at least one of one or more historical image datasets or one or more simulated image datasets and an output of the scatter correction model comprises a scatter correction.

Any of the aspects herein, wherein the scatter correction model averages two or more image datasets of the plurality of image datasets.

Any of the aspects herein, wherein the second robotic arm orients the detector independent of the first robotic arm.

Any of the aspects herein, wherein the memory saves further data configured to cause the processor to: calculate a magnification factor based on each image dataset of the plurality of image datasets and the corresponding source detector distance, and scale the initial image using the magnification factor.

Any of the aspects herein, wherein the source detector distance is determined by subtracting a pose of the source from a pose of the detector.

Any of the aspects herein, wherein the pose of the source and the pose of the detector may be determined from pose information received from a first sensor of the first robotic arm and a second sensor of the second robotic arm.

Any of the aspects herein, wherein the plurality of second poses are at a same elevation.

Any of the aspects herein, wherein the imaging device is an X-ray device.

A system for generating a corrected image according to at least one embodiment of the present disclosure comprises a first robotic arm configured to orient a source of an X-ray device at a first pose; a second robotic arm configured to orient a detector of the X-ray device at a plurality of second poses, wherein each second pose and the first pose define a source detector distance extending between the source and the detector; at least one processor; and a memory storing data for processing by the processor, the data, when processed, causing the processor to: receive an image dataset from the detector at each of the plurality of second poses to yield a plurality of image datasets, the plurality of datasets comprising an initial image having a scatter effect; determine a scatter correction configured to correct a scatter effect; and applying the correction to the initial image to correct the scatter effect.

Any of the aspects herein, wherein determining the scatter correction includes determining a first set of photons and a second set of photons, the first set of photons corresponding to un-scattered photons and the second set of photons corresponding to scattered photons.

Any of the aspects herein, wherein the memory saves further data configured to cause the processor to: calculate a magnification factor based on each image dataset of the plurality of image datasets and the corresponding source detector distance, and scale the initial image using the magnification factor.

Any of the aspects herein, wherein the memory saves further data configured to cause the processor to: train a model using a Monte-Carlo simulation to simulate a plurality of photon paths that forms an image, the image being at least one of a historical image or a simulated image, wherein determining the scatter correction uses the trained model.

Any of the aspects herein, wherein training the model uses the plurality of image datasets to yield a scatter correction.

Any of the aspects herein, wherein determining the scatter correction comprises providing the image dataset to a trained scatter correction model.

Any of the aspects herein, wherein the scatter correction model is trained using a plurality of image datasets and an output of the scatter correction model comprises a scatter correction.

A device for generating a corrected image according to at least one embodiment of the present disclosure comprises at least one processor; and a memory storing data for processing by the processor, the data, when processed, causing the processor to: receive an image dataset from an imaging device having a source at a first pose and a detector at a second pose of a plurality of second poses, the image dataset received at each second pose of the plurality of second poses to yield a plurality of image datasets, the plurality of datasets comprising an initial image having a scatter effect, wherein each second pose and the first pose define a source detector distance extending between the source and the detector; save the plurality of image datasets; determine a scatter correction configured to correct a scatter effect; and applying the correction to the initial image to correct the scatter effect.

A system for generating a corrected image according to at least one embodiment of the present disclosure comprises an imaging device comprising a source configured to emit a wave and a detector configured to receive a signal indicative of the emitted wave; a first robotic arm configured to orient the source at a first pose; a second robotic arm configured to orient the detector at a plurality of second poses, wherein each second pose and the first pose define an angle between the source and the detector and a source detector distance extending between the source and the detector; at least one processor; and a memory storing data for processing by the processor, the data, when processed, causes the processor to: receive an image dataset from the detector at each of the plurality of second poses to yield a plurality of image datasets, the plurality of datasets comprising an initial image having a scatter effect; save the plurality of image datasets; determine a scatter correction configured to correct the scatter effect; and applying the correction to the initial image to correct the scatter effect.

Any of the aspects herein, wherein the image is a three-dimensional image and the correction corrects the scatter effect for a volume.

Any of the aspects herein, wherein the memory saves further data configured to cause the processor to: train a scatter correction model using a Monte-Carlo simulation to simulate a plurality of photon paths that forms an image, the image being at least one of a historical image or a simulated image, wherein determining the scatter correction uses the trained model.

Any of the aspects herein, wherein determining the scatter correction comprises providing the image dataset to a trained scatter correction model.

Any of the aspects herein, wherein the scatter correction model is trained using a plurality of image datasets and an output of the scatter correction model comprises a scatter correction.

Any of the aspects herein, wherein the scatter correction model is trained using at least one of one or more historical image datasets or one or more simulated image datasets and an output of the scatter correction model comprises a scatter correction.

Any of the aspects herein, wherein the scatter correction model averages two or more image datasets of the plurality of image datasets.

Any of the aspects herein, wherein the memory saves further data configured to cause the processor to: calculate a magnification factor based on each image dataset of the plurality of image datasets and the corresponding source detector distance, and scale the initial image using the magnification factor.

Any of the aspects herein, wherein the angle and the source detector distance is determined by subtracting a pose of the source from a pose of the detector.

Any of the aspects herein, wherein the pose of the source and the pose of the detector may be determined from pose information received from a first sensor of the first robotic arm and a second sensor of the second robotic arm.

Any of the aspects herein, wherein the plurality of second poses are at different elevations.

Any of the aspects herein, wherein the imaging device is an X-ray device.

A system for generating a corrected image according to at least one embodiment of the present disclosure comprises an imaging device comprising a source configured to emit a wave and a detector configured to receive a signal indicative of the emitted wave; a first robotic arm configured to orient the source at a one or more first poses; a second robotic arm configured to orient the detector at a plurality of second poses, wherein each second pose and each first pose define an angle between the imaging device and an object and a source detector distance extending between the source and the detector; at least one processor; and a memory storing data for processing by the processor, the data, when processed, causes the processor to: receive an image dataset from the detector where the source is at each of the one or more first poses and the detector is at each of the plurality of second poses to yield a plurality of image datasets, the plurality of datasets comprising an initial image having a scatter effect; save the plurality of image datasets; determine a scatter correction configured to correct the scatter effect; and applying the correction to the initial image to correct the scatter effect.

Any of the aspects herein, wherein the image is a three-dimensional image and the correction corrects the scatter effect for a volume.

Any of the aspects herein, wherein determining the scatter correction includes determining a first set of photons and a second set of photons, the first set of photons corresponding to un-scattered photons and the second set of photons corresponding to scattered photons.

Any of the aspects herein, wherein the memory saves further data configured to cause the processor to: calculate a magnification factor based on each image dataset of the plurality of image datasets and the corresponding source detector distance, and scale the initial image using the magnification factor.

Any of the aspects herein, wherein training the model uses the plurality of image datasets to yield a scatter correction.

Any of the aspects herein, wherein determining the scatter correction comprises providing the image dataset to a trained scatter correction model.

Any of the aspects herein, wherein the scatter correction model is trained using a plurality of image datasets and an output of the scatter correction model comprises a scatter correction.

A system for generating a corrected image according to at least one embodiment of the present disclosure comprises an imaging device comprising a source configured to emit a wave and a detector configured to receive a signal indicative of the emitted wave; a first robotic arm configured to orient the source at a one or more first poses, wherein for each first pose, the source is positioned at a different angle relative to an object; a second robotic arm configured to orient the detector at a plurality of second poses for each first pose of the one or more first poses, wherein at each second pose the detector is at a different angle relative to the source and at a different source detector distance defined by a distance between the detector and the source; at least one processor; and a memory storing data for processing by the processor, the data, when processed, causes the processor to: receive an image dataset from the detector where the source is at each of the one or more first poses and the detector is at each of the plurality of second poses to yield a plurality of image datasets, the plurality of datasets comprising an initial three-dimensional image having a scatter effect; save the plurality of image datasets; determine a scatter correction configured to correct the scatter effect; and applying the correction to the initial three-dimensional image to correct the scatter effect.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 5 is a flowchart according to at least one embodiment of the present disclosure.

DETAILED DESCRIPTION

Figure 1:
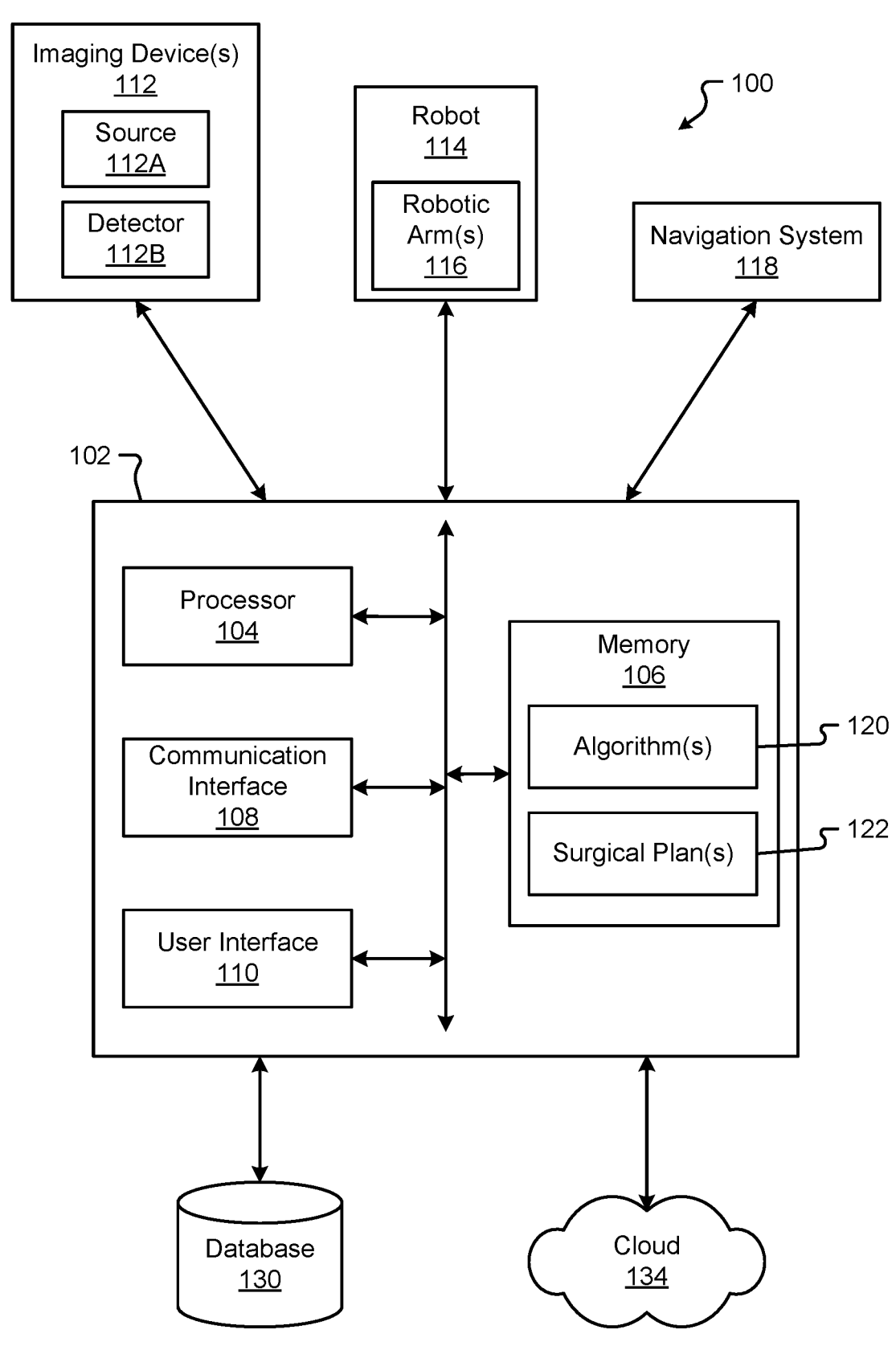
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions or algorithms may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

X-ray based imaging may be affected by scatter that occurs when photons hit an object along their path and change direction. As a result, the photons reach another area of the detector than expected and misrepresents a true attenuation of a scanned object. Such stray photons may also reduce the contrast of an image and/or increase a blurriness of the image.

Conventional ways to reduce scatter include using hardware such as, for example, anti-scatter grids. Such grids may be beam-stop-arrays, which are placed on the detector itself, and are made of many thin "walls" in a grid shape that attenuates most of the photons that are not perpendicular to the detector. However, such grids typically result in an increased X-ray dose to the patient, and may lose accuracy or functionality in poor conditions. Thus, another conventional solution uses software. Such solutions attempt to estimate from the "scattered" image, an "un-scattered" object. This is usually done by one of two methods: using Monte-Carlo simulations or deep learning techniques. The Monte-Carlo simulations work on many synthetic models, with different sizes and shapes. The Monte-Carlo simulations simulate the photon path while considering various sorts of physical conditions and restrictions. Later, when scanning a target object, the scatter can be estimated from the model and can apply a correction on the X-ray projection (e.g., image) to reduce the scatter. However, most of the corrections rely on a "predetermined" model, and very little on the actual target object.

The deep learning techniques may also use many phantom or real clinical cases, which were scanned with and without anti-scatter grids. The deep learning techniques may also use Monte-Carlo simulations as input. Such deep learning techniques may improve a run-time performance. The system learns the difference between the un-scattered and scattered images and applies the necessary correction on the new projection without the grid, to look as if it was taken with a grid. For such techniques, many scans are used with and without the grid, on the specific system, which may not always be available.

At least one embodiment of the present disclosure includes a system that uses multiple robotic arms that can take images in any orientations and in different positions of an object. Such system may take a couple of frames of the scanned object from the same orientation, only with a different source detector distance (SDD). In other instances, the frames may be taken at different SDDs, at different angles of the detector relative to the source, and/or at different angles of the detector and the source relative to the object. Assuming a still object, and the same scan protocol, the differences between the projections can be used to determine the scaling of the object due to magnification and a scatter.

The magnification can be easily calculated, according to the known arms (source and detector) position and distances in each of the frames. Hence the other difference would be a result of the scatter. This scatter can be estimated by means of image processing and applied in conjunction with the other software options. Now the estimation would depend more on the actual scanned object, and less on predefined models, or general models. The magnification and/or the estimated scatter can be applied to the image, whether a 2D image or a 3D image, to correct the scatter in the image. The results would be more tailored and a better representation of the object. Such improved images can result in a better volume\image reconstruction and improved clinical outcome.

Embodiments of the present disclosure provide technical solutions to one or more of the problems of (1) obtaining multiple image datasets at various source detector distances, various angles of a detector relative to a source, and/or various angles of the detector and the source relative to an object, (2) improving image processing to reduce or eliminate scatter, and (3) increasing patient safety by reducing radiation exposure.

Turning first to FIG. 1, a block diagram of a system 100 according to at least one embodiment of the present disclosure is shown. The system 100 may be used to generate a corrected image (whether 2D or 3D) and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400 and/or 500 described herein, or of any other methods. The memory 106 may store, for example, one or more algorithms 120 and/or one or more surgical plans 122. Such algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as algorithms, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient.

In some embodiments, the imaging device 112 may comprise more than one imaging device 112. For example, a first imaging device may provide first image data and/or a first image at a first time, and a second imaging device may provide second image data and/or a second image at the first time or at a second time after the first time. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

In some embodiments, the imaging device 112 may comprise a source 112A and a detector 112B. In some embodiments, the source 112A and the detector 112B may be in separate housings or are otherwise physically separated. In such embodiments, the source 112A may be oriented by a first robotic arm and the detector 112B may be oriented by a second robotic arm, as will be described in more detail below. In other embodiments, the source 112A and the detector 112B may be in the same housing. The source 112A may be configured to emit a wave and the detector 112B may be configured to receive a signal indicative of the emitted wave. The detector 112B may also be configured to save a plurality of image datasets to, for example, the memory 106. The wave may be, for example, an X-ray wave.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure.

Figures 2A, 2B:
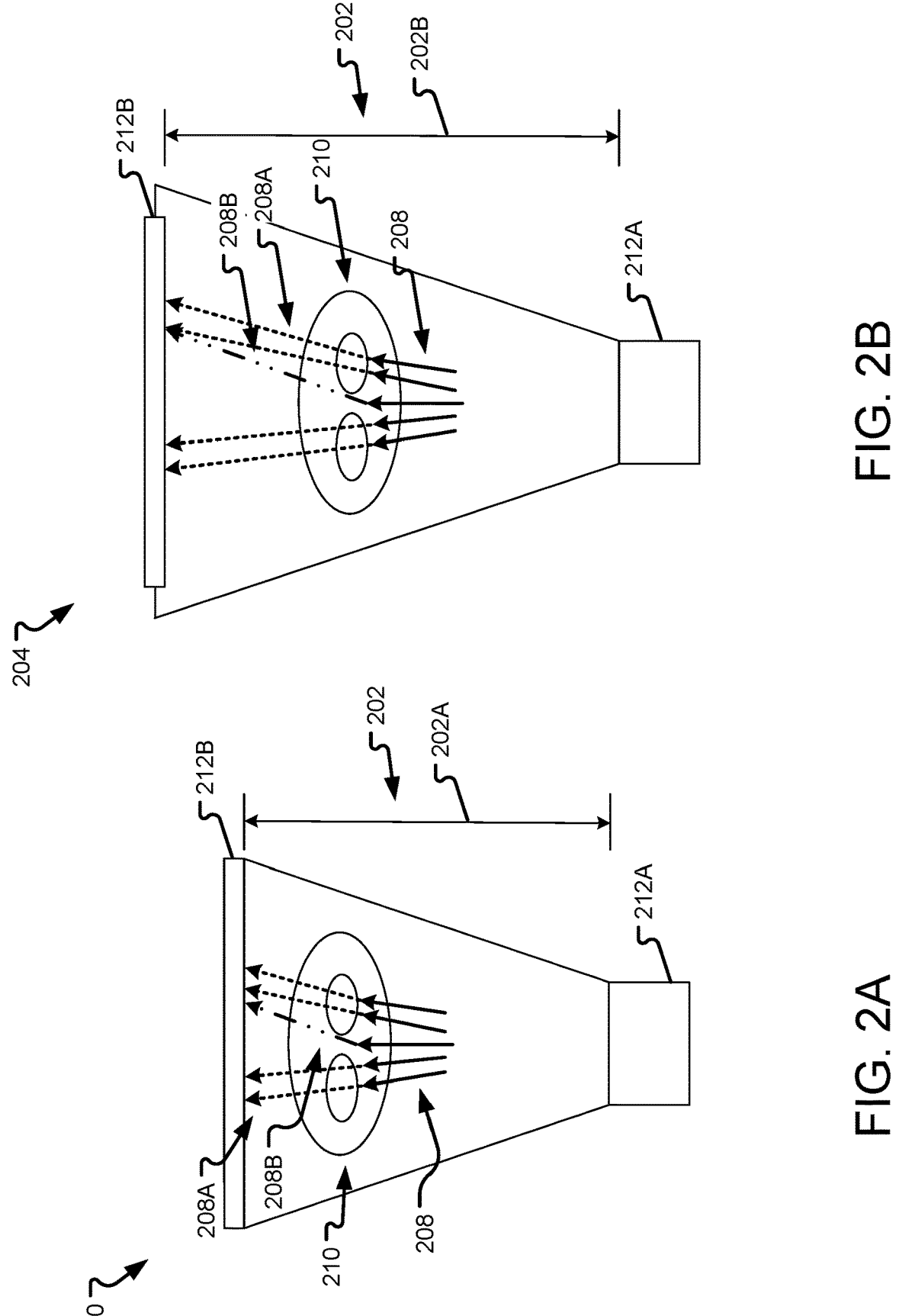
FIG. 2A is a schematic diagram of capturing image data at a first distance according to at least one embodiment of the present disclosure.
FIG. 2B is a schematic diagram of capturing image data at a second distance according to at least one embodiment of the present disclosure.

The robot 114 may comprise one or more robotic arms 116. The robotic arms may be controlled in a single, shared coordinate space, or in separate coordinate spaces. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components such as, for example, the source 112A and the detector 112B, one robotic arm 116 may hold the source 112A, and another robotic arm 116 may hold the detector 112B. Each robotic arm 116 may be accurately positionable independently of the other robotic arm (e.g., the detector 112B can be positioned or oriented independently of the source 112A). In some embodiments, one robotic arm 116 may orient the source 112A at a first pose across from the detector 112B oriented by another robotic arm 116 at a second pose. A distance between the source 112A and the detector 112B may be referred to as a source detector distance ("SDD") 202, as shown in FIGS. 2A-2B. The robotic arms 116 may be operable to orient the source 112A and the detector 112B at one or more SDDs 202. In some embodiments, the source 112A may remain at the same pose while the detector 112B is oriented at different poses. In other embodiments, the detector 112B may remain at the same pose while the source 112A is oriented at different poses. In still other embodiments, both the detector 112B and the source 112B may each be oriented at different poses relative to each other and/or relative to the object.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store, for example, one or more surgical plans 122 (including, for example, pose information for an imaging device 112; steps to capture one or more image datasets; one or more settings for an imaging device 112, etc.); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 400 and/or 500 described herein. The system 100 or similar systems may also be used for other purposes.

Turning to FIGS. 2A and 2B, a schematic diagram 200 of capturing image data at a first SDD 202A and another schematic diagram 204 of capturing image data at a second SDD 202B are respectively depicted. In the illustrated examples, a source 212A—which may be the same as or similar to the source 112A—is spaced from a detector 212B—which may be the same as or similar to the detector 212B at an SDD 202. Further, as shown, one or more objects (e.g., surgical instruments, tools, surgical implants, existing implants, etc.) and/or one or more anatomical elements 210 are positioned between the source 212A and the detector 212B. Such one or more objects and/or one or more anatomical elements 210 may be depicted by the resulting image datasets obtained from the source 212A and the detector 212B. During use, the source 212A emits a wave (which may be, for example, an X-ray wave) comprising a plurality of photons 208 that passes through the one or more objects and/or one or more anatomical elements 210 and the detector 212B receives a signal indicative of the plurality of photons 208.

As shown in FIGS. 2A and 2B, some of the plurality of photons 208 may maintain a straight line through the one or more objects and/or one or more anatomical elements 210 and will be referred to as straight or un-scattered photons 208A (depicted as a dashed line). As further illustrated in FIGS. 2A and 2B, straight photons or un-scattered 208A maintain a straight line through the one or more objects and/or one or more anatomical elements 210 regardless of the SDD 202. The un-scattered photons 208A may be easily identified in image datasets taken at different SDDs 202. On the other hand, some of the plurality of photons 208 may not maintain a straight line through the one or more objects and/or one or more anatomical elements 210 and will be referred to as scattered photons 208B (depicted as a dash-double dot line). Scattered photons 208B may refract or become skewed and exit the one or more objects and/or one or more anatomical elements 210 at an angle and may be received by the detector 212B at a random or different position. Such scattered photons 208B can create a scatter effect in an image which may be visible as, for example, noise, a change in contrast, and/or an increase in blurriness of the image.

Straight or un-scattered photons 208A may be predictable in where they may be received by the detector 212B whereas scattered photons 208B may be less predictable in where they may be received by the detector 212B. By taking multiple image datasets at various SDDs 202, the un-scattered photons 208A and at least some of the scattered photons 208B may be identified by observing a relationship between the photons 208 in each image dataset.

Also shown in FIGS. 2A and 2B, are an image dataset taken at a first SDD 202A and an image dataset taken at a second SDD 202B. The second SDD 202B is greater than the first SDD 202A, though the second SDD 202B in some instances may be less than the first SDD 202A. In the illustrated embodiment, the second SDD 202B (or any other SDD) is obtained by keeping the source 212A stationary and orienting the detector 212B (by, for example, a robotic arm such as the robotic arm 116) at a distance further away from the source 212A than the first SSD 202A. In such embodiments, the detector 212B remains at the same orientation. It will be appreciated that in other embodiments, the detector 212B may be oriented at a different orientation. In other embodiments, the second SDD 202B (or any other SDD) may be obtained by keeping the detector 212B stationary while the source 212A is oriented at a different distance and/or orientation from the detector 212B. In still other embodiments, the second SDD 202B (or any other SDD) may be obtained by orienting both the detector 212B and the source 212A at different distances and/or orientations from each other.

As will be described in detail below with respect to FIGS. 4 and 5, by obtaining two or more image datasets at two or more SDDs 202, a magnification factor may be calculated based on the known SDDs 202 and the resultant straight or un-scattered photons 208A as received by the detector 212B. Further, a scatter correction may be determined from the image datasets. The scatter correction may also be obtained as output from a scatter correction model using the image datasets as input, which will be described in detail with respect to FIGS. 3-5.

Figures 2C, 2D:
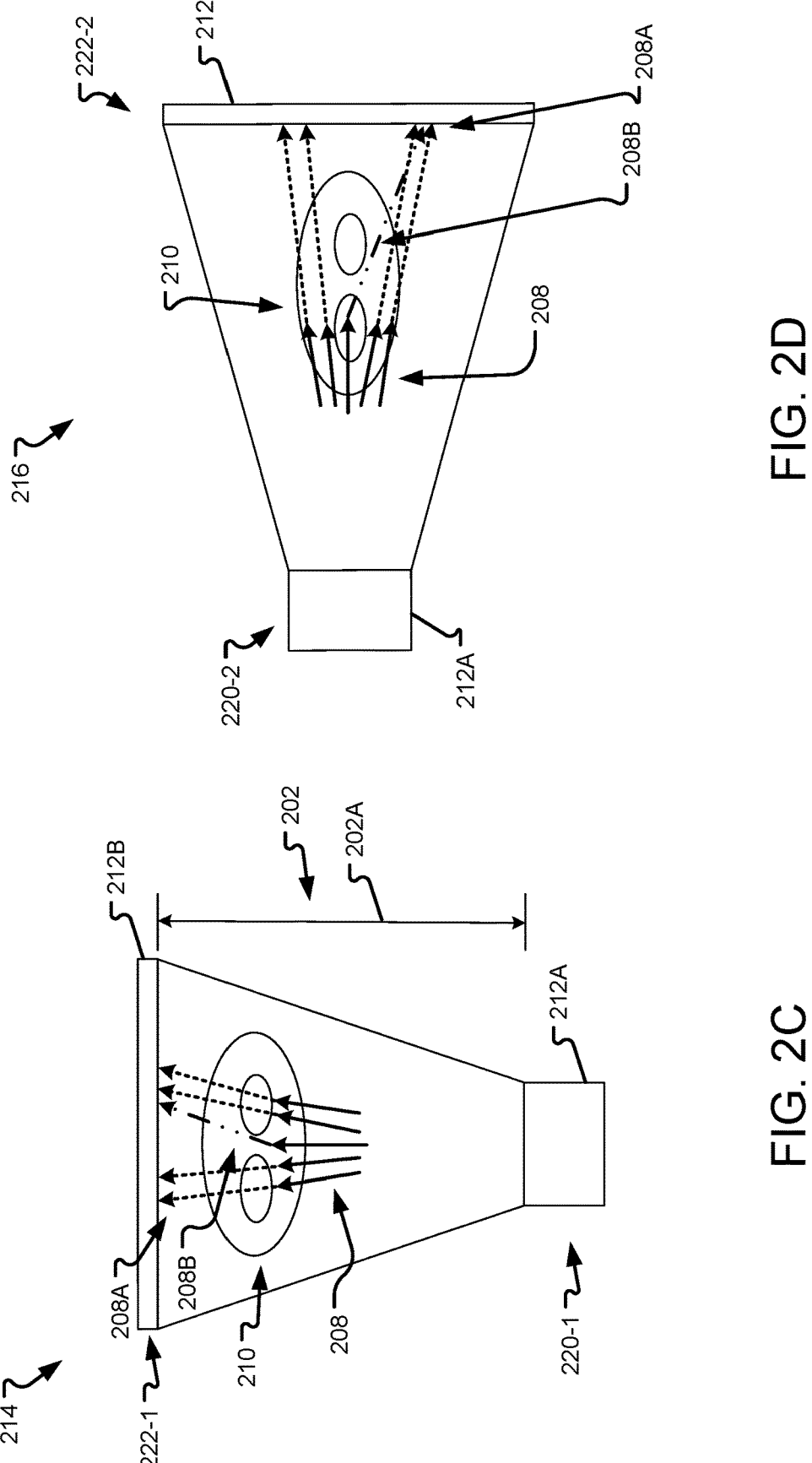
FIG. 2C is a schematic diagram of capturing image data at a first distance and a first angle relative to an object according to at least one embodiment of the present disclosure.
FIG. 2D is a schematic diagram of capturing image data at a second distance and a second angle relative to the object according to at least one embodiment of the present disclosure.

Turning to FIGS. 2C and 2D, a schematic diagram 214 of capturing image data where the source 212A is at a pose 220-1 of one or more first poses and the detector 212B is at a pose 222-1 of a plurality of second poses and another schematic diagram 216 of capturing image data where the source 212A is at another pose 220-2 of the one or more first poses and the detector 212B is at another pose 222-2 of the plurality of second poses are respectively depicted. In the illustrated examples, the source 212A—which may be the same as or similar to the source 112A—is spaced from the detector 212B—which may be the same as or similar to the detector 212B at the SDD 202. As described above and as shown, one or more objects (e.g., surgical instruments, tools, surgical implants, existing implants, etc.) and/or one or more anatomical elements 210 are positioned between the source 212A and the detector 212B. Such one or more objects and/or one or more anatomical elements 210 may be depicted by the resulting image datasets obtained from the source 212A and the detector 212B. During use, the source 212A emits a wave (which may be, for example, an X-ray wave) comprising the plurality of photons 208 that passes through the one or more objects and/or one or more anatomical elements 210 and the detector 212B receives a signal indicative of the plurality of photons 208. The plurality of photons may be straight or unscattered photons 208A or may be scattered photons 208B.

As shown in FIGS. 2C and 2D, an image dataset is taken where the source 212A is at pose 220-1 of the one or more first poses and the detector 212B is at pose 222-1 of the plurality of second poses and where the source 212A is at pose 220-2 of the one or more first poses and the detector 212B is at pose 222-2 of the plurality of second poses. As shown, the pose 220-1 of the one or more first poses is different than the pose 220-2 of the one or more first poses and the pose 222-1 of the plurality of second poses is different than the pose 222-2 of the plurality of second poses. In other words, the source 212A and the detector 212B may be at different poses relative to the anatomical element 210 when image dataset(s) are taken. It will be appreciated that in such embodiments where the source 212A and the detector 212B are at different poses relative to the anatomical element 210 when the image dataset(s) are obtained, the source 212A and the detector 212B may also be at different SDDs 202 for a given first pose of the source 212A. In other words, the source 212A may be positioned at one pose of the one or more first poses, then an image dataset may be taken with the detector 212B at different SDDs 202 where the detector 212B is positioned at various poses of a plurality of second poses. The source 212B may be then positioned at another pose of the one or more first poses, then another image dataset may be taken with the detector 212B at different SDDs 202 where the detector 212B is positioned at various poses of a plurality of second poses. It will be appreciated that any number of image dataset may be taken for any number of one or more first poses and/or second poses.

In another example, as will be described below, the source 212A may be positioned at one pose of a one or more first poses, then an image dataset may be taken with the detector 212B at different SDDs 202 and/or at different angles relative to the source 212A where the detector 212B is positioned at various poses of a plurality of second poses. The source 212B may be then positioned at another pose of the one or more first poses, then another image dataset may be taken with the detector 212B at different SDDs 202 and/or at different angles relative to the source 212A where the detector 212B is positioned at various poses of a plurality of second poses (whether the same poses or different poses as the poses of the detector 202B when the source 202A is at the one pose of the one or more first poses). It will be appreciated that in some embodiments the source 212A may be positioned at one pose and then an image dataset may be taken with the detector 212B at different SDDs 202 and/or at different angles relative to the source 212A.

By taking image datasets where the source 212A and the detector 212B (e.g., the imaging device 112) are positioned at different angles relative to the object, a correction may be generated and applied to a volume. Additionally or alternatively, by taking image datasets where the detector 212B is positioned at different SDDs 202 and/or angles relative to the source 212A, the accuracy of the correction as estimated from the scatter may be increased.

As will be described in detail below with respect to FIGS. 4-6, by obtaining two or more image datasets at two or more SDDs 202, a magnification factor may be calculated based on the known SDDs 202 and the resultant straight or un-scattered photons 208A as received by the detector 212B. Further, a scatter correction may be determined from the image datasets. The scatter correction may also be obtained as output from a scatter correction model using the image datasets as input, which will be described in detail with respect to FIGS. 3-6.

Figure 2E:
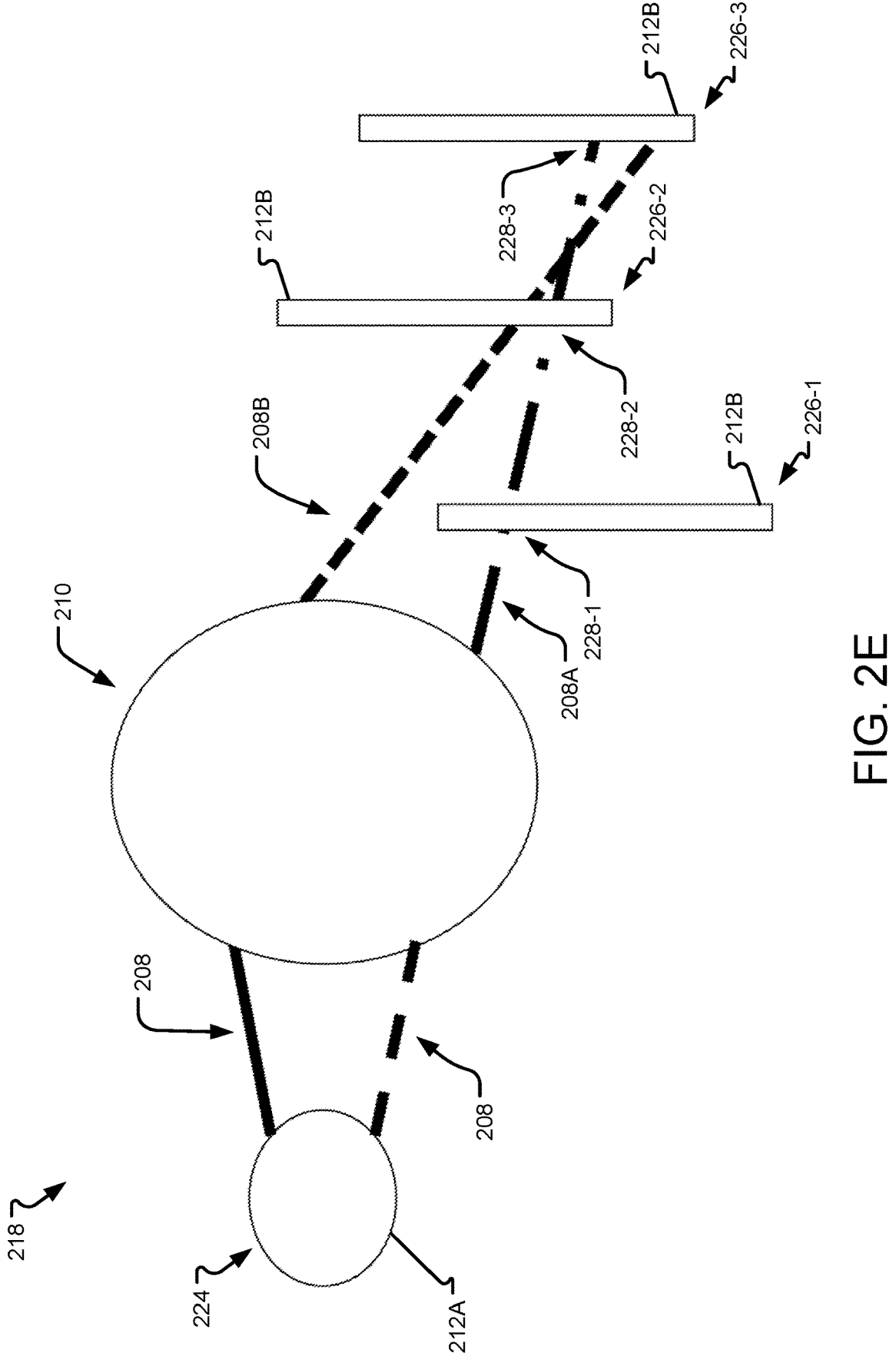
FIG. 2E is a schematic diagram of capturing image data at different distances and angles according to at least one embodiment of the present disclosure.

Turning to FIG. 2E, a schematic diagram 218 of capturing image data where the source 212A is at a pose 224 and the detector 212B is at poses 226-1, 226-2, 226-3 of a plurality of second poses is depicted. As previously described, the source 212A—which may be the same as or similar to the source 112A—is spaced from the detector 212B—which may be the same as or similar to the detector 212B. As also described above, one or more objects (e.g., surgical instruments, tools, surgical implants, existing implants, etc.) and/ or one or more anatomical elements 210 are positioned between the source 212A and the detector 212B. Such one or more objects and/or one or more anatomical elements 210 may be depicted by the resulting image datasets obtained from the source 212A and the detector 212B. During use, the source 212A emits a wave (which may be, for example, an X-ray wave) comprising a plurality of photons 208 that passes through the one or more objects and/or one or more anatomical elements 210 and the detector 212B receives a signal indicative of the plurality of photons 208. The plurality of photons may be straight or unscattered photons 208A or may be scattered photons 208B.

As illustrated, the detector 212B may be positioned at poses 226-1, 226-2, 226-3 of the plurality of second poses such that the detector 212B is positioned at different angles relative to the source 212A and at different SDDs 202. In such embodiments, the detector 212B is positioned such that the plurality of straight or unscattered photons 208A will intersect the detector 212B at different points 228-1, 228-2, 228-3. Because the detector 212B is positioned at different angles relative to the source 212A, random noise (e.g., scatter) can be measured at the different points 228-1, 228-2, 228-3, which can then be cancelled out by using a method such as, for example averaging the random noise measured.

Figure 3:
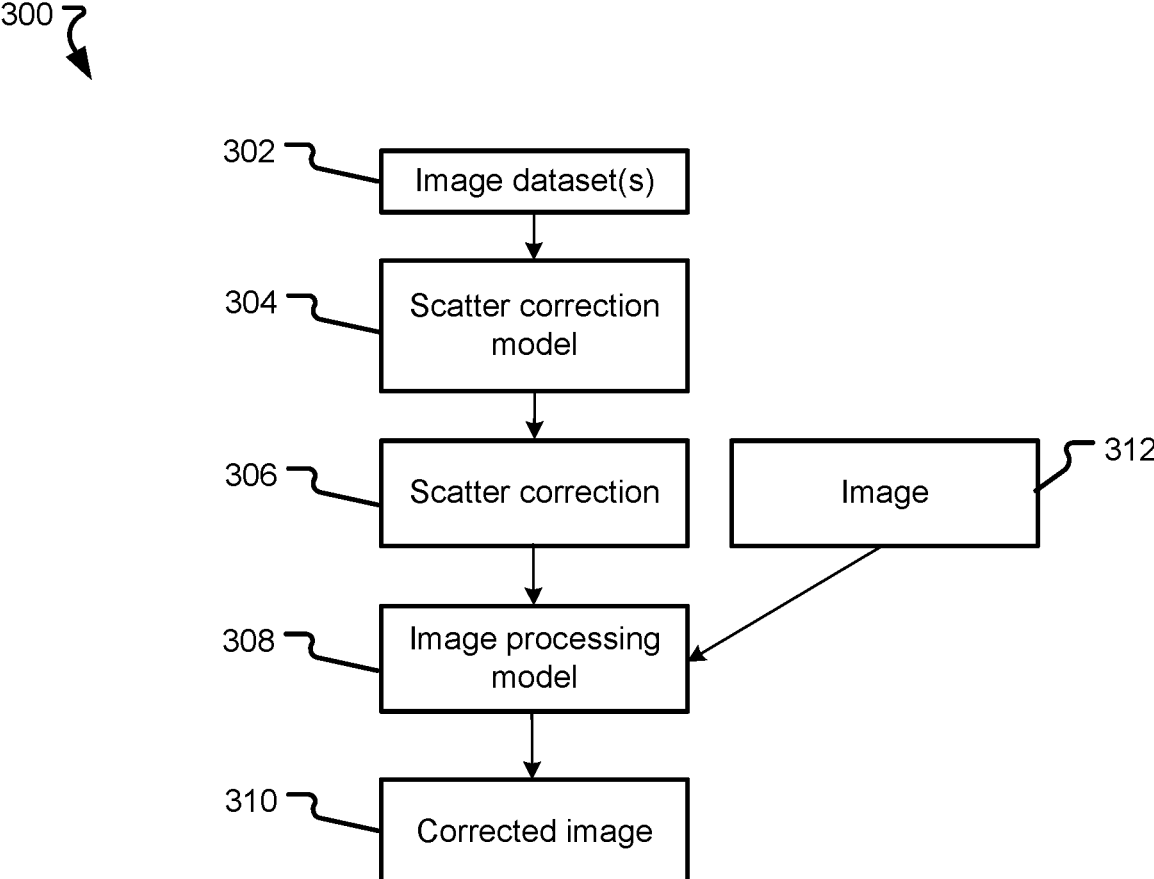
FIG. 3 is a flowchart according to at least one embodiment of the present disclosure.

Turning to FIG. 3, an example of a model architecture 300 that supports methods and systems (e.g., Artificial Intelligence (AI)-based methods and/or system) for generating a corrected image is shown.

One or more image datasets 302 may be obtained by an imaging device such as the imaging device 112 comprising a source such as the source 112A, 212A and a detector such as the detector 112B, 212B that are oriented across from each other at a corresponding one or more SDDs such as the SDDs 202. Each of the image datasets 302 may depict one or more objects and/or one or more anatomical elements of, for example, a patient. The plurality of image datasets 302 may comprise an initial image having a scatter effect.

The one or more image datasets 302 are received as input by a scatter correction model 304. The scatter correction model 304 may be trained using one or more sets of historical image datasets, wherein at least some sets of historical image data may contain a plurality of known photon paths of a different, historical patient. In other embodiments, the scatter correction model 304 may be trained using the one or more image datasets 302. In still other embodiments, the scatter correction model 304 may be trained using image(s) obtained from a simulation (e.g., a Monte-Carlo simulation, for example). In such embodiments, the scatter correction model 304 may be trained prior to inputting the one or more image datasets 302 into the scatter correction model 304 or may be trained in parallel with inputting the one or more image dataset 302 into the scatter correction model 304. The scatter correction model 304 may be configured determine a scatter correction 306, which may be applied to an image, such as the initial image, to correct a scatter effect.

The scatter correction 306 and an image 312 from the plurality of image dataset may be used by a processor such as the processor 104 as input for an image processing model 308. The image processing model 308 may output a corrected image 310, which may be free of or substantially free of the scatter effect. In some embodiments, the image 312 may be the initial image of the plurality of image datasets. The image processing model 308 may apply the scatter correction 306 to the initial image, or any image with a scatter effect, to output the corrected image 310. In other embodiments, the image processing model 308 may output a newly generated image free or substantially free of the scatter effect.

The image processing model 308 may be trained using historical scatter corrections and historical images having historical scatter effects. In other embodiments, the image processing model 308 may be trained using the image 312 (which may be, for example, the initial image of the one or more image datasets 302) and the scatter correction 306. In such embodiments, the image processing model 308 may be trained prior to inputting the scatter correction 306 and the image 312 into the scatter correction model 304 or may be trained in parallel with inputting the scatter correction 306 and the image 312 into the image processing model 308.

Figure 4:
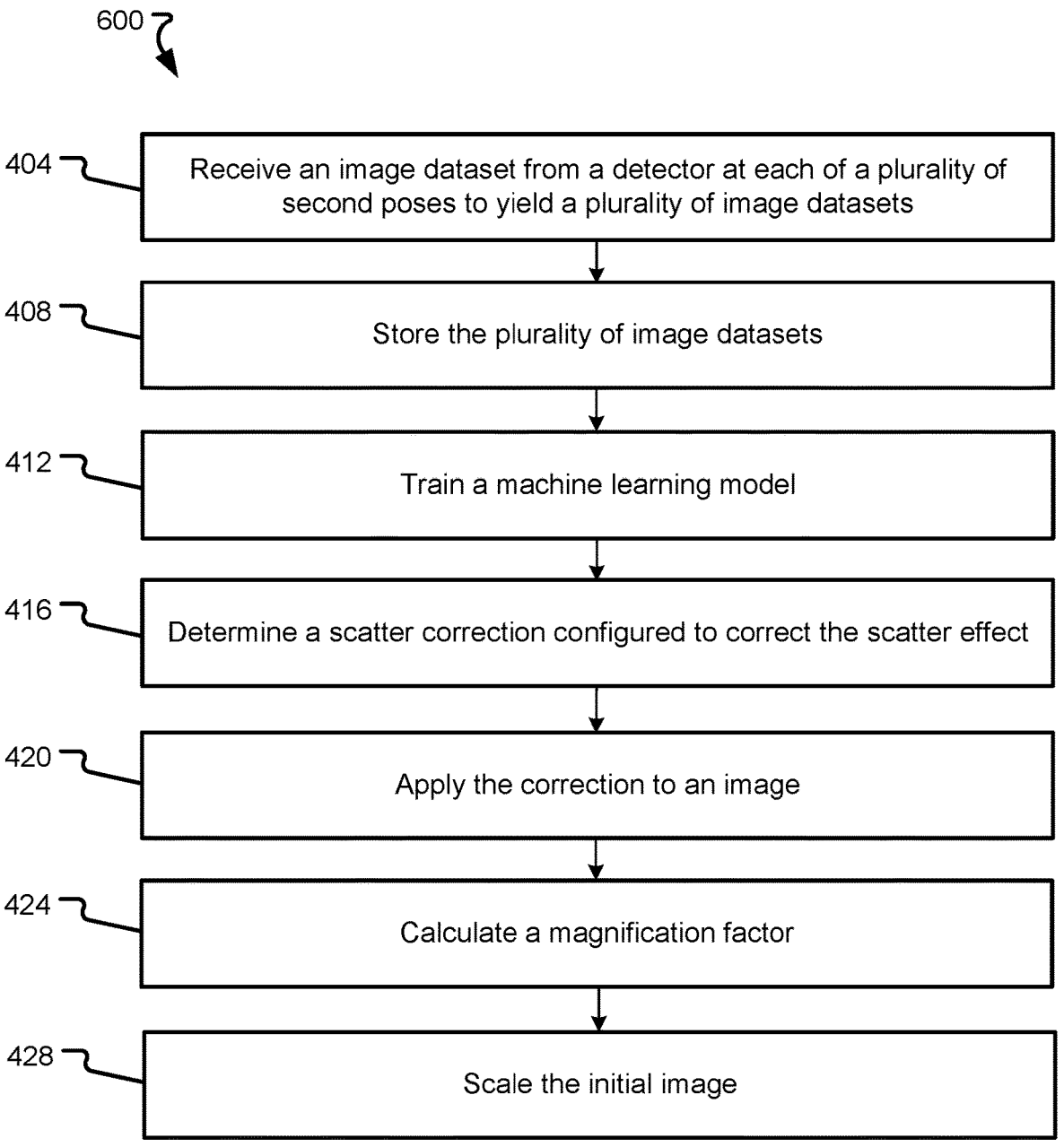
FIG. 4 is a flowchart according to at least one embodiment of the present disclosure.

FIG. 4 depicts a method 400 that may be used, for example, for generating a corrected image.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as the algorithm 120.

The method 400 comprises receiving an image dataset from a detector at each of a plurality of second poses (step 404). The detector may be the same as or similar to the detector 112B, 212B of an imaging device such as the imaging device 112. In some embodiments, the imaging device is an X-ray device. The imaging device may also comprise a source as the source 112A, 212A configured to emit a wave. The detector may be configured to receive a signal indicative of the emitted wave. The source may be oriented by a first robotic arm such as the robotic arm 116 at a first pose and the detector may be oriented by a second robotic arm such as the robotic arm 116 at the plurality of second poses. In some embodiments, the plurality of second poses are each at the same elevation. The first robotic arm may orient the source independently of the second robotic arm orienting the detector, and vice versa. Each of the plurality of second poses and the first pose define a source detector distance (SDD) such as the SDD 202 extending between the source and the detector.

In some embodiments, the plurality of second poses and the first pose may be obtained from a surgical plan such as the surgical plan 122. In other embodiments, the plurality of second poses and the first pose may be input received by a user such as a surgeon or other medical provider. In still other embodiments, the plurality of second poses and the first pose may be determined by a processor such as the processor 104 based on settings of the imaging device, settings of one or more robotic arms, one or more objects and/or one or more anatomical elements being imaged, or the like. Receiving an image dataset from the detector at each of the plurality of second poses yields a plurality of image datasets. The plurality of image datasets may define an initial image having a scatter effect.

The method 400 also comprises saving the plurality of image datasets (step 408). The plurality of image datasets may be saved by a processor such as the processor 104 to a memory such as the memory 106. The processor and/or the memory may be part of the imaging device, a computing device such as the computing device 102, or separate from the imaging device and/or the computing device. The plurality of image datasets may, in some embodiments, depict one or more anatomical elements. In other embodiments, the plurality of image datasets may depict one or more objects and/or one or more anatomical elements.

The method 400 also comprises training a scatter correction model (step 412). The scatter correction model may be the same as or similar to the scatter correction model 304. An output of the scatter correction model comprises a scatter correction such as the scatter correction 306, which may be used to correct a scatter effect of an image. The scatter correction model is trained using a plurality of image datasets, which may be historical image datasets, simulated image datasets, and/or current image datasets. In some embodiments, training the machine learning model may use a Monte-Carlo simulation to simulate a plurality of photon paths that forms an image. The image may be a historical image and/or a simulated image. The simulated image may be, for example, one or more images obtained from a Monte-Carlo simulation.

The method 400 also comprises determining a scatter correction configured to correct the scatter effect (step 416). The scatter correction may be the same as or similar to the scatter correction 306. Determining the scatter correction may use the scatter correction model trained in step 412. In such embodiments, the plurality of image datasets received in step 404 are received as input by the scatter correction model and an output of the scatter correction model is the scatter correction.

The scatter correction model may, in some embodiments, operate by averaging two or more images of the plurality of image datasets to determine a scatter correction. In other embodiments, the scatter correction model may determine a first set of photons and a second set of photons. The first set of photons may correspond to un-scattered photons (such as, for example, the un-scattered photons 208A) and the second set of photons corresponding to scattered photons (such as, for example, the scatter photons 208B). The scatter correction model may then determine the scatter correction based on first set of photons and the second set of photons.

It will be appreciated that in other embodiments, determining the scatter correction may not use the scatter correction model trained in step 412.

The method 400 also comprises applying the scatter correction to an image (step 420). The image may be, for example, the initial image of the plurality of image datasets having a scatter effect. Applying the scatter correction to the initial image may result in correcting a scatter effect in the initial image, which may be visible as a reduction or elimination of, for example, noise and/or blurriness in the initial image. A contrast of the initial image may also be improved.

In some embodiments, applying the scatter correction uses an image processing model such as the image processing model 308. In such instances, the image and the scatter correction may be used as input by a processor such as the processor 104 to the image processing model. The image processing model may output a corrected image, which may be free of or substantially free of the scatter effect.

The method 400 also comprises calculating a magnification factor (step 424). The magnification factor may be based on each image dataset of the plurality of image datasets and the corresponding SDD. In some embodiments, the SDD may be determined by subtracting a pose of the source from a pose of the detector. In some embodiments, the pose of the source may be determined from pose information received from a first sensor of a first robotic arm orienting the source and the pose of the detector may be determined from pose information received from a second sensor of a second robotic arm orienting the detector. In other embodiments, the SDD may be received from a surgical plan such as the surgical plan 122. In still other embodiments, the SDD may be input received from a user such as a surgeon or other medical provider.

The method 400 also comprises scaling the image (step 428). The image may be, for example, the initial image, the corrected image, or any image with or without a scatter effect. Scaling the image may comprise scaling the image using the magnification factor calculated in step 424.

It will be appreciated that in some embodiments, the steps 424 and 428 may occur simultaneously with steps 416 and/or 420. In other words, the scatter correction may be applied to the image (such as, for example, the initial image) and the image may be scaled simultaneously. In other embodiments, the image may be scaled prior to applying the scatter correction or vice versa.

The present disclosure encompasses embodiments of the method 400 that comprise more or fewer steps than those described above, and/or one or more steps that are different than the steps described above.

FIG. 5 depicts a method 500 that may be used, for example, for generating a corrected image.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as the algorithm 120.

The method 500 comprises receiving an image dataset from a detector where a source is positioned at a pose of one or more first poses and the detector is positioned at each of a plurality of second poses to yield a plurality of image datasets (step 504). The detector may be the same as or similar to the detector 112B, 212B of an imaging device such as the imaging device 112. In some embodiments, the imaging device is an X-ray device. The imaging device may also comprise a source as the source 112A, 212A configured to emit a wave. The detector may be configured to receive a signal indicative of the emitted wave.

The step 504 may be the same as or similar to the step 404 of the method 400 described above except that the source may be oriented by a first robotic arm such as the robotic arm 116 at each or one of the one or more first poses and the detector may be oriented by a second robotic arm such as the robotic arm 116 at each of the plurality of second poses. The first robotic arm may orient the source independently of the second robotic arm orienting the detector, and vice versa.

As previously described, in at least one embodiment, the source may be positioned at one pose of the one or more first poses, then an image dataset may be taken with the detector at various pose of the plurality of second poses such that the detector is at different SDDs such as the SDDs 202 and/or at different angles relative to the source. The source may be then positioned at another pose of the one or more first poses, then another image dataset may be taken with the detector at different SDDs and/or at different angles relative to the source where the detector is positioned at various poses of a plurality of second poses (whether the same poses or different poses as the poses of the detector 202B when the source 202A is at the one pose of the one or more first poses).

It will be appreciated that in some embodiments the source may be positioned at one pose and then an image dataset may be taken with the detector at different SDDs and/or at different angles relative to the source.

The method 500 also comprises saving the plurality of image datasets (step 508). The step 508 may be the same as or similar to the step 408 of the method 400 described above.

The method 500 also comprises training a scatter correction model (step 512). The step 512 may be the same as or similar to the step 412 of the method 400 described above.

The method 500 also comprises determining a scatter correction configured to correct the scatter effect (step 516). The step 516 may be the same as or similar to the step 416 of the method 400 described above.

The method 500 also comprises applying the scatter correction to an image (step 520). The step 508 may be the same as or similar to the step 408 of the method 400 described above. It will be appreciated that the image may be a 2D image or a 3D image. In instances where the image is a 3D image, the scatter correction may be applied to a volume such that scatter depicted in the volume may be corrected.

The method 500 also comprises calculating a magnification factor (step 524). The step 524 may be the same as or similar to the step 424 of the method 400 described above.

The method 500 also comprises scaling the image (step 528). The step 528 may be the same as or similar to the step 428 of the method 400 described above.

It will be appreciated that in some embodiments, the steps 524 and 528 may occur simultaneously with steps 516 and/or 520. In other words, the scatter correction may be applied to the image (such as, for example, the initial image) and the image may be scaled simultaneously. In other embodiments, the image may be scaled prior to applying the scatter correction or vice versa.

The present disclosure encompasses embodiments of the method 500 that comprise more or fewer steps than those described above, and/or one or more steps that are different than the steps described above. As noted above, the present disclosure encompasses methods with fewer than all of the steps identified in FIGS. 4-5 (and the corresponding description of the methods 400 and 500), as well as methods that include additional steps beyond those identified in FIGS. 4-5 (and the corresponding description of the methods 400 and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for generating a corrected image, comprising:
an imaging device comprising a source configured to emit a wave and a detector configured to receive a signal indicative of the emitted wave;
a first robotic arm configured to orient the source at a first pose;
a second robotic arm configured to orient the detector at a plurality of second poses, wherein each second pose and the first pose define an angle between the source and the detector and a source detector distance extending between the source and the detector;
at least one processor; and
a memory storing data for processing by the at least one processor, the data, when processed, causes the at least one processor to:
receive an image dataset from the detector at each of the plurality of second poses to yield a plurality of image datasets, the plurality of image datasets comprising an initial image having a scatter effect;
save the plurality of image datasets;
determine a scatter correction configured to correct the scatter effect; and
apply the scatter correction to the initial image to correct the scatter effect.

2. The system of claim 1, wherein the initial image is a three-dimensional image and the scatter correction corrects the scatter effect for a volume.

3. The system of claim 1, wherein the memory includes further data configured to cause the at least one processor to:
train a scatter correction model using a Monte-Carlo simulation to simulate a plurality of photon paths that form at least one of a historical image or a simulated image, wherein determining the scatter correction uses the trained scatter correction model.

4. The system of claim 1, wherein determining the scatter correction comprises providing the image dataset to a trained scatter correction model.

5. The system of claim 4, wherein the scatter correction model is trained using a plurality of input image datasets, and wherein an output of the scatter correction model comprises the scatter correction.

6. The system of claim 5, wherein the scatter correction model averages two or more input image datasets of the plurality of input image datasets.

7. The system of claim 4, wherein the scatter correction model is trained using at least one of one or more historical image datasets or one or more simulated image datasets, and wherein an output of the scatter correction model comprises the scatter correction.

8. The system of claim 1, wherein the memory includes further data configured to cause the at least one processor to:
calculate a magnification factor based on each image dataset of the plurality of image datasets and the corresponding source detector distance; and
scale the initial image using the magnification factor.

9. The system of claim 8, wherein the angle and the source detector distance is determined by subtracting a pose of the source from a pose of the detector.

10. The system of claim 9, wherein the pose of the source and the pose of the detector is determined from pose information received from a first sensor of the first robotic arm and a second sensor of the second robotic arm.

11. The system of claim 1, wherein the plurality of second poses are at different elevations.

12. The system of claim 1, wherein the imaging device is an X-ray device.

13. A system for generating a corrected image, comprising:
an imaging device comprising a source configured to emit a wave and a detector configured to receive a signal indicative of the emitted wave;
a first robotic arm configured to orient the source at a one or more first poses;
a second robotic arm configured to orient the detector at a plurality of second poses, wherein each second pose and each first pose define an angle between the imaging device and an object and a source detector distance extending between the source and the detector;
at least one processor; and
a memory storing data for processing by the at least one processor, the data, when processed, causes the at least one processor to:
receive an image dataset from the detector where the source is at each of the one or more first poses and the detector is at each of the plurality of second poses to yield a plurality of image datasets, the plurality of image datasets comprising an initial image having a scatter effect;
save the plurality of image datasets;
determine a scatter correction configured to correct the scatter effect; and
apply the scatter correction to the initial image to correct the scatter effect.

14. The system of claim 13, wherein the initial image is a three-dimensional image and the scatter correction corrects the scatter effect for a volume.

15. The system of claim 13, wherein determining the scatter correction includes determining a first set of photons and a second set of photons, the first set of photons corresponding to un-scattered photons and the second set of photons corresponding to scattered photons.

16. The system of claim 13, wherein the memory includes further data configured to cause the at least one processor to:
calculate a magnification factor based on each image dataset of the plurality of image datasets and the corresponding source detector distance; and
scale the initial image using the magnification factor.

17. The system of claim 16, wherein the memory includes further data configured to cause the at least one processor to:
train a scatter correction model using a Monte-Carlo simulation to simulate a plurality of photon paths that form at least one of a historical image or a simulated image.

18. The system of claim 16, wherein determining the scatter correction comprises using a trained scatter correction model.

19. The system of claim 18, wherein the scatter correction model is trained using a plurality of input image datasets and an output of the scatter correction model comprises the scatter correction.

20. A system for generating a corrected image comprising:

an imaging device comprising a source configured to emit a wave and a detector configured to receive a signal indicative of the emitted wave;

a first robotic arm configured to orient the source at one or more first poses, wherein for each first pose, the source is positioned at a different angle relative to an object;

a second robotic arm configured to orient the detector at a plurality of second poses for each first pose of the one or more first poses, wherein at each second pose the detector is at a different angle relative to the source and at a different source detector distance defined by a distance between the detector and the source;

at least one processor; and a memory storing data for processing by the at least one processor, the data, when processed, causes the at least one processor to:

receive an image dataset from the detector where the source is at each of the one or more first poses and the detector is at each of the plurality of second poses to yield a plurality of image datasets, the plurality of image datasets comprising an initial three-dimensional image having a scatter effect;

save the plurality of image datasets;

determine a scatter correction configured to correct the scatter effect; and apply the scatter correction to the initial three-dimensional image to correct the scatter effect.

\* \* \* \* \*